(12) United States Patent
Yamada et al.

(10) Patent No.: US 10,227,318 B2
(45) Date of Patent: Mar. 12, 2019

(54) METHOD FOR PRODUCING GAMMA-VALEROLACTONE

(71) Applicant: UBE INDUSTRIES, LTD., Ube-shi, Yamaguchi (JP)

(72) Inventors: Atsushi Yamada, Ube (JP); Yasushi Yamamoto, Ube (JP)

(73) Assignee: UBE INDUSTRIES, LTD., Yamaguchi (JP)

( * ) Notice: Subject to any disclaimer, the term of this patent is extended or adjusted under 35 U.S.C. 154(b) by 0 days.

(21) Appl. No.: 15/766,381

(22) PCT Filed: Sep. 6, 2016

(86) PCT No.: PCT/JP2016/076137
§ 371 (c)(1),
(2) Date: Apr. 6, 2018

(87) PCT Pub. No.: WO2017/085986
PCT Pub. Date: May 26, 2017

(65) Prior Publication Data
US 2018/0297972 A1    Oct. 18, 2018

(30) Foreign Application Priority Data
Nov. 16, 2015  (JP) ................. 2015-224093

(51) Int. Cl.
| C07D 307/00 | (2006.01) |
| C07D 307/33 | (2006.01) |
| B01J 23/46 | (2006.01) |
| C07B 61/00 | (2006.01) |

(52) U.S. Cl.
CPC .......... C07D 307/33 (2013.01); B01J 23/462 (2013.01); B01J 23/464 (2013.01); B01J 23/468 (2013.01); B01J 23/46 (2013.01); C07B 61/00 (2013.01)

(58) Field of Classification Search
CPC .... C07D 307/33; C07D 315/00; B01J 23/892; B01J 23/72; B01J 23/8966; B01J 23/80; B01J 23/755; B01J 23/04; B01J 21/04; B01J 21/063; B01J 21/066; B01J 21/08; B01J 21/12
USPC ................................ 549/295, 326
See application file for complete search history.

(56) References Cited

U.S. PATENT DOCUMENTS 4,420,622 A * 12/1983 van de Moesdijk ......... C07D 315/00
549/295
5,883,266 A   3/1999 Elliott et al.

| 2003/0055270 A1 | 3/2003 | Manzer |
| 2006/0162239 A1 | 7/2006 | Van Den Brink et al. |
| 2011/0046399 A1 | 2/2011 | Haan et al. |
| 2012/0329981 A1 | 12/2012 | Castelijns et al. |

FOREIGN PATENT DOCUMENTS

| CN | 102658131 A | 9/2012 |
| EP | 1 292 555 B1 | 3/2004 |
| JP | 2003-535916 A | 12/2003 |
| JP | 2005-500987 A | 1/2005 |
| JP | 2008-525372 A | 7/2008 |
| JP | 2014-166604 A | 9/2014 |
| JP | 2014-524905 A | 9/2014 |
| JP | 2015-074619 A | 4/2015 |
| WO | 2015/026234 A1 | 2/2015 |

OTHER PUBLICATIONS

Official Communication issued in International Patent Application No. PCT/JP2016/076137, dated Dec. 13, 2016.
Luo et al., "High performing and stable supported nano-alloys for the catalytic hydrogenation of levulinic acid to gamma-valerolactone", Nature Communications, Article No. 6540, Mar. 17, 2015, pp. 1-10.
Li et al., "FeSBA-15-supported ruthenium catalyst for the selective hydrogenolysis of carboxylic acids to alcoholic chemicals", Catalysis Today, vol. 251, Aug. 1, 2015, pp. 53-59.
Yang et al., "Facile Fabrication of Composition-Tuned Ru—Ni Bimetallics in Ordered Mesoporous Carbon for Levulinic Acid Hydrogenation", ACS Catalysis, vol. 4, No. 5, 2014, pp. 1419-1425.
Al-Naji et al., "Insights into the selective hydrogenation of levulinic acid to gamma-valerolactone using supported mono-and bimetallic catalysts", Journal of Molecular Catalysis A: Chemical, vol. 417, Mar. 5, 2016, pp. 145-152.
English Translation of Official Communication issued in International Patent Application No. PCT/JP2016/076137, dated May 31, 2018.

\* cited by examiner

*Primary Examiner* — Taylor V Oh
(74) *Attorney, Agent, or Firm* — Keating and Bennett, LLP

(57) ABSTRACT

Provided is a method for producing γ-valerolactone that is hard to elute metallic components and has high productivity. γ-Valerolactone is synthesized by bringing a levulinic acid compound represented by the formula (1) (where R represents a hydrogen atom, a linear alkyl group of 1 to 6 carbon atoms or a branched alkyl group of 3 to 6 carbon atoms) into contact with hydrogen in the presence of a catalyst in which two or more different kinds of metals of Group VIII to Group X metals in the periodic table are supported on a support.

[Chem. 1]

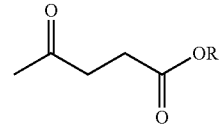

(1)

4 Claims, No Drawings

METHOD FOR PRODUCING GAMMA-VALEROLACTONE

TECHNICAL FIELD

The present invention relates to a method for producing γ-valerolactone.

BACKGROUND ART

Conventional methods for producing γ-valerolactone by bringing a levulinic acid compound into contact with hydrogen, for example, the following methods.

For an example, Patent Literature 1 describes a method for producing γ-valerolactone by reacting levulinic acid or its ester with hydrogen in the presence of a carbonyl complex of ruthenium or iron.

For another example, Patent Literature 2 describes a method for producing γ-valerolactone by reacting levulinic acid with hydrogen in the presence of an iridium-, palladium-, platinum-, rhenium-, rhodium- or ruthenium-supported catalyst.

For still another example, Patent Literature 3 describes a method for producing γ-valerolactone by reacting levulinic acid with hydrogen in the presence of a ruthenium catalyst supported on activated carbon and 0.08% water relative to levulinic acid by weight.

For still another example, Patent Literature 4 describes a method for producing γ-valerolactone by reacting levulinic acid or its ester with hydrogen in the presence of an oxide composite made of copper oxide and aluminum oxide.

CITATION LIST

Patent Literature

Patent Literature 1: JP-A-2003-535916
Patent Literature 2: JP-A-2005-500987
Patent Literature 3: JP-A-2014-524905
Patent Literature 4: JP-A-2014-166604

SUMMARY OF INVENTION

Technical Problem

However, the method of Patent Literature 1 has a problem that the product is difficult to recover because the catalyst is a homogeneous catalyst, and a problem that the productivity is poor because the reaction time is long.

The inventors conducted reproductive experiments on the methods of Patent Literatures 2 and 3. As a result, it was confirmed that metallic components were eluted and the catalytic activity was obviously decreased (see Comparative Example 1 described below). And the similar results are described in comparative examples in Patent Literature 4.

Further, the method of Patent Literature 4 has a problem that the productivity is poor because the yield of γ-valerolactone is low.

The main subject of the present invention is to provide a method for producing γ-valerolactone that is hard to elute metallic components and has high productivity.

Solution to Problem

A method for producing γ-valerolactone according to the present invention includes bringing a levulinic acid compound represented by the following formula (1),

[Chem. 1]

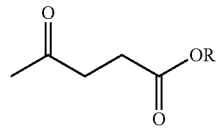

(1)

where R represents a hydrogen atom, a linear alkyl group of 1 to 6 carbon atoms or a branched alkyl group of 3 to 6 carbon atoms, contact with hydrogen in the presence of a catalyst in which two or more different kinds of metals of Group VIII to Group X metals in the periodic table are supported on a support, thus synthesizing γ-valerolactone.

Advantageous Effects of Invention

The present invention enables provision of a method for producing γ-valerolactone that is hard to elute metallic components and has high productivity.

DESCRIPTION OF EMBODIMENTS

Hereinafter, the expression "reaction for obtaining γ-valerolactone by bringing a levulinic acid compound into contact with hydrogen in the present invention" is also referred to as "reaction of the present invention". Furthermore, the expression "catalyst for use in the reaction of the present invention" is also referred to as "catalyst of the present invention" or simply as "catalyst".

(Catalyst)

The catalyst for use in the present invention is a "catalyst in which two or more different kinds of metals of Group VIII to Group X metals in the periodic table are supported on a support".

Examples of Group VIII to Group X metals in the periodic table that can be preferably used include iron, ruthenium, osmium, cobalt, rhodium, iridium, nickel, palladium, and platinum, more preferred are ruthenium, rhodium, iridium, palladium, and platinum, and still more preferred are ruthenium, iridium, and platinum.

Preferred examples of a combination of the above metals include:
a combination of ruthenium and iridium;
a combination of ruthenium and platinum;
a combination of ruthenium, iridium, and one or more kinds of metals of Group VIII to Group X metals (exclusive of ruthenium and iridium) in the periodic table; and
a combination of ruthenium, platinum, and one or more kinds of metals of Group VIII to Group X metals (exclusive of ruthenium and platinum) in the periodic table.

In the catalyst of the present invention, the above mentioned metals are supported on the support so that the amount of each kind of metal is preferably 0.1 to 15% by mass and more preferably 1 to 8% by mass. The total amount of the two or more kinds of metals supported on the support is preferably 0.2 to 30% by mass and more preferably 2 to 16% by mass. It can be supposed that when the amount of metal or metals supported on the support is within the above ranges, the elution of the metallic components can be reduced and the catalytic activity tends to be retained for a long time.

(Support)

The porous support is preferably used as the support in the catalyst and specific examples thereof include porous silica, porous alumina, porous silica-alumina (aluminosilicate), porous ceria, porous magnesia, porous calcia, porous titania, porous silica-titania (titanosilicate), porous zirconia, activated carbon, zeolite, and mesoporous materials (mesoporous alumina, mesoporous silica, and mesoporous carbon). Preferably used are porous silica, porous alumina, porous activated carbon, and porous zeolite.

These supports may be used alone or two or more of them may be used.

(Synthesis of Catalyst)

The catalyst of the present invention can be synthesized, for example, by the following method. First, the support is impregnated with a solution (for example, an aqueous solution) of a "metallic compound" containing below-mentioned "two or more different kinds of metals of Group VIII to Group X metals in the periodic table" and dried. The drying temperature is preferably 60° C. to 200° C. and more preferably 100° C. to 150° C.

In addition, the impregnation with the solution of a metallic compound may be performed at a time using a mixture solution containing two or more different kinds of metals or the support may be sequentially subjected to processes each including impregnation with one of solutions of two or more different kinds of metallic compounds and drying.

Subsequently, the support is subjected to calcinating preferably at 50° C. to 800° C. and more preferably at 100° C. to 600° C. or like methods, so that the catalyst of the present invention can be obtained.

The amount of metallic compound containing two or more kinds of metals used can be appropriately selected according to the amount of metals to be supported on the support. The total mass of metallic compound is, per gram of the support, preferably 0.01 to 0.3 g and more preferably 0.02 to 0.16 g.

The catalyst of the present invention is preferably subjected to reduction treatment. The reduction treatment can be conducted in the stage of production of the catalyst, before the catalyst is mixed with a levulinic acid compound or after the catalyst is mixed with a levulinic acid compound, but the reduction treatment for the catalyst of the present invention is preferably conducted just before the reaction of the present invention is preformed from the viewpoint of developing high catalytic activity.

The method for the reduction treatment is not limited particularly so long as it is a method of bringing the catalyst into contact with a reductant. For example, the method of bringing the catalyst into contact with hydrogen is preferably used because the reaction of the present invention uses hydrogen.

(Metallic Compound)

Examples of metallic compounds preferably used in the present invention include:

iron compounds, such as iron chloride, iron bromide, iron iodide, iron fluoride, iron nitrate, iron oxide, iron phosphate, and iron acetate;

ruthenium compounds, such as ruthenium trichloride, ruthenium tribromide, diammonium ruthenium pentachloride, triammonium ruthenium hexachloride, dipotassium ruthenium hexachloride, disodium ruthenium hexachloride, tripotassium ruthenium hexabromide, and dipotassium ruthenium hexabromide;

osmium compounds, such as osmium trichloride, osmium tribromide, diammonium osmium pentachloride, triammonium osmium hexachloride, dipotassium osmium hexachloride, disodium osmium hexachloride, tripotassium osmium hexabromide, and dipotassium osmium hexabromide;

cobalt compounds, such as cobalt dichloride, cobalt dibromide, cobalt diiodide, cobalt difluoride, cobalt dinitrate, cobalt oxide, cobalt phosphate, and cobalt diacetate;

rhodium compounds, such as rhodium trichloride, triammonium rhodium hexachloride, tripotassium rhodium hexachloride, trisodium rhodium hexachloride, and rhodium trinitrate;

iridium compounds, such as iridium trichloride, iridium tribromide, iridium tetrachloride, iridium tetrabromide, ammonium iridate, hexaammineiridium trichloride, pentaamminechloroiridium dichloride, triammonium iridium hexachloride, tripotassium iridium hexachloride, trisodium iridium hexachloride, diammonium iridium tetrachloride, diammonium iridium hexachloride, dipotassium iridium hexachloride, hexachloroiridic acid, and disodium iridium hexachloride;

nickel compounds, such as nickel dichloride, nickel dibromide, and nickel diiodide;

palladium compounds, such as palladium dichloride, palladium dibromide, palladium diiodide, palladium diacetate, palladium dinitrate, palladium sulfate, and palladium oxide; and platinum compounds, such as platinum dichloride, platinum tetrachloride, hexachloroplatinic acid, platinum dibromide, platinum tetrabromide, hexabromoplatinic acid, platinum diiodide, platinum tetraiodide, diammonium platinum dichloride, diammonium platinum hexachloride, diammonium platinum hexachloride, diammonium platinum tetrachloride, disodium platinum hexachloride, dipotassium platinum tetrachloride, dipotassium platinum hexachloride, diammonium platinum dibromide, dipotassium platinum tetrabromide, diammonium platinum hexabromide, sodium hexaiodoplatinate, potassium hexaiodoplatinate, platinum oxide, and hexahydroxoplatinic acid.

(Method for Producing γ-Valerolactone)

In the present invention, γ-valerolactone is produced by reacting a levulinic acid compound represented by the following formula (1) with hydrogen in the presence of the above-described catalyst:

[Chem. 2]

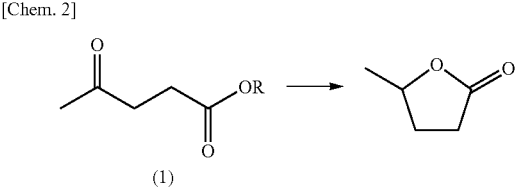

(1)

where R represents a hydrogen atom, a linear alkyl group of 1 to 6 carbon atoms or a branched alkyl group of 3 to 6 carbon atoms.

(Levulinic Acid Compound)

A levulinic acid compound for use in the reaction of the present invention is a compound represented by the above formula (1). In the formula (1), R represents a hydrogen atom, a linear alkyl group of 1 to 6 carbon atoms or a branched alkyl group of 3 to 6 carbon atoms. Examples of the linear alkyl group of 1 to 6 carbon atoms include methyl group, ethyl group, n-propyl group, n-butyl group, n-pentyl group, and n-hexyl group. Examples of the branched alkyl group of 3 to 6 carbon atoms include isopropyl group, isobutyl group, tert-butyl group, and sec-butyl group.

These levulinic acid compounds can be obtained from lignocellulosic biomass. When a biomass-derived levulinic acid compound is used, the resultant γ-valerolactone is an entirely plant-derived material.

In the reaction of the present invention, either a batch manner or a continuous manner can be selected depending on the form of the catalyst. Furthermore, the reaction of the present invention can be performed in either a homogeneous reaction system or a heterogeneous reaction (suspension reaction) system depending on the property of the catalyst. By using the catalyst supported on a support, the reaction of the present invention can be continuously performed on a fixed bed reaction system.

In performing the reaction of the present invention in a batch manner, the reaction is performed, for example, while the catalyst and levulinic acid are mixed and stirred in a hydrogen atmosphere.

In performing the reaction of the present invention in a continuous manner, the reaction is performed, for example, while hydrogen and a levulinic acid compound are allowed to flow through a reaction tube filled with the catalyst. As necessary, an inert solid infill supporting the filling of the catalyst into the reactor may be disposed in the reactor.

The reaction temperature during which the above-described reaction is performed is preferably 50° C. to 220° C. and more preferably 80° C. to 200° C. Furthermore, the reaction pressure is, in terms of hydrogen partial pressure, ordinary pressure to 10 MPa and more preferably ordinary pressure to 5 MPa.

The above reaction temperature and reaction pressure may be changed intermittently or continuously within their respective ranges. When the reaction temperature and reaction pressure are within the above ranges, γ-valerolactone as an objective substance can be obtained at a high reaction rate and a high yield and highly selectively while the production of side products is suppressed.

In the reaction of the present invention, a solvent may be used for ease of supply of the levulinic acid compound, improvement in stirrability in a batch manner, improvement in flowability in a continuous manner or other purposes. The type of the solvent is not limited particularly so long as it does not inhibit the reaction, and examples include water; alcohols, such as methanol, ethanol, n-propyl alcohol, isopropyl alcohol, n-butyl alcohol, tert-butyl alcohol, and ethylene glycol; hydrocarbons, such as heptane, hexane, cyclohexane, and toluene; amides, such as N,N-dimethylfolmamide, N,N-dimethylacetamide, and N-methyl-2-pyrrolidone; ethers, such as diethyl ether, diisopropyl ether, 1,2-dimethoxyethane, 1,2-diethoxyethane, diethylene glycol dimethyl ether, diethylene glycol diethyl ether, tetrahydrofuran, and dioxane; and halogenated hydrocarbons, such as methylene chloride, dichloroethane, and chlorocyclohexane. Water, alcohols, hydrocarbons, and ethers are preferably used and water is more preferably used. These solvents may be used alone or two or more of them may be used in mixture.

The amount of the above solvent used is, per gram of levulinic acid compound, preferably 0 g to 100 g and more preferably 0 g to 50 g. When the amount of solvent used is within these ranges, stirring or flow can be rapidly performed to smoothly promote the reaction.

As a result of the reaction of the present invention, a desired levulinic acid compound can be obtained. Specifically, this levulinic acid compound can be isolated and refined, from the reaction solution obtained after the end of the reaction, by a general operation, for example, filtration, condensation, extraction, distillation, sublimation, recrystallization or column chromatography.

The preferred embodiment of the present invention has been heretofore described, but the present invention is not limited to the above embodiment.

EXAMPLES

Next, the present invention will be described concretely with examples, but the scope of the present invention is not limited to these examples.

Example 1 (Production of Catalyst)

An amount of 4.30 g of activated carbon (granular Shirasagi C2X 8/12 manufactured by Japan EnviroChemicals, Ltd.) was impregnated with an aqueous solution obtained by dissolving 0.560 g of iridium(III) chloride n-hydrate (1.6 mmol, manufactured by Sigma-Aldrich) in 8.0 g of 1 mol/L hydrochloric acid, and the whole was dried at 110° C. for 12 hours.

Next, the resultant solid was impregnated with an aqueous solution obtained by diluting 3.70 g of potassium ruthenate (VI) solution (ruthenium content: 4.32% by mass, 1.6 mmol, manufactured by Furuya Metal Co., Ltd.) with 5.0 g of water, and the whole was dried at 110° C. for 12 hours and then fired at 200° C. for 4 hours, thus obtaining 4.82 g of catalyst (hereinafter, also referred to as "Ru—Ir/AC catalyst") in which 3.3% ruthenium and 6.3% iridium were supported on activated carbon.

Example 1-A (Synthesis of γ-Valerolactone) A reaction tube (10 mm diameter×100 mm long) was filled with 2.0 mL of catalyst (Ru—Ir/AC catalyst) (Ru: 0.31 mmol, Ir: 0.31 mmol) produced in Example 1 and further filled, on top of the catalyst, with 4.0 mL of glass beads of 2 mm size as a preheating layer. The reaction tube was heated at 200° C. for two hours by a heater while hydrogen was supplied at 20 mL/min. Thereafter, 20.0% by mass levulinic acid aqueous solution was supplied at a rate of 70 mg/min into the reaction tube while hydrogen was supplied at a rate of 5.0 mL/min, and a liquid from the exit of the reaction tube was collected.

Analysis of the collected liquid one hour after the start of the reaction showed that the conversion rate of levulinic acid was 100% and the yield of γ-valerolactone was 99.9%. The reaction was subsequently performed and analysis of the collected liquid 40 hours after the start of the reaction showed that the conversion rate of levulinic acid was 97.6% and the yield of γ-valerolactone was 96.6%.

Comparative Example 1 (Synthesis of γ-Valerolactone)

Reaction was performed in the same manner as in Example 1 except that in Example 1 the catalyst to be filled was 2.0 mL of pellet-like 5% by mass Ru/AC catalyst (Ru: 0.52 mmol) (manufactured by N. E. Chemcat Corporation).

Analysis of the collected solution one hour after the start of the reaction showed that the conversion rate of levulinic acid was 86.4% and the yield of γ-valerolactone was 86.3%. The reaction was subsequently performed and analysis of the collected liquid 16 hours after the start of the reaction showed that the conversion rate of levulinic acid was 48.2% and the yield of γ-valerolactone was 47.7%.

Example 2 (Production of Catalyst)

An amount of 4.30 g of activated carbon (granular Shirasagi C2X 8/12 manufactured by Japan EnviroChemicals, Ltd.) was impregnated with an aqueous solution obtained by dissolving 0.560 g of iridium(III) chloride n-hydrate (1.6 mmol, manufactured by Sigma-Aldrich) and 0.422 g of ruthenium(III) chloride n-hydrate (1.6 mmol, manufactured by Wako Pure Chemical Industries, Ltd.) in 8.0 g of 1 mol/L hydrochloric acid, and the whole was dried at 110° C. for 12 hours and then fired at 200° C. for four hours, thus obtaining 4.66 g of catalyst (hereinafter, also referred to as "Ru—Ir/AC (2) catalyst") in which 3.5% ruthenium and 6.6% iridium were supported on activated carbon.

Example 2-A (Synthesis of γ-Valerolactone)

Reaction was performed in the same manner as in Example 1 except that the catalyst to be filled was 2.0 mL of Ru—Ir/AC (2) catalyst (Ru: 0.31 mmol, Ir: 0.31 mmol) prepared in Example 2.

Analysis of the collected solution one hour after the start of the reaction showed that the conversion rate of levulinic acid was 100% and the yield of γ-valerolactone was 98.8%. The reaction was subsequently performed and analysis of the collected liquid 40 hours after the start of the reaction showed that the conversion rate of levulinic acid was 100% and the yield of γ-valerolactone was 96.2%.

Example 3 (Production of Catalyst)

An amount of 4.30 g of activated carbon (granular Shirasagi C2X 8/12 manufactured by Japan EnviroChemicals, Ltd.) was impregnated with an aqueous solution obtained by dissolving 0.422 g of ruthenium(III) chloride n-hydrate (1.6 mmol, manufactured by Wako Pure Chemical Industries, Ltd.) and 0.593 g of platinum(IV) chloride (1.6 mmol, manufactured by Wako Pure Chemical Industries, Ltd.) in 8.0 g of 1 mol/L hydrochloric acid, and the whole was dried at 110° C. for 12 hours and then fired at 200° C. for four hours, thus obtaining 4.78 g of catalyst (hereinafter, also referred to as "Ru—Pt/AC (1) catalyst") in which 3.4% ruthenium and 6.5% platinum were supported on activated carbon.

Example 3-A (Synthesis of γ-Valerolactone)

Reaction was performed in the same manner as in Example 1 except that the catalyst to be filled was 2.0 mL of Ru—Pt/AC (1) catalyst (Ru: 0.31 mmol, Pt: 0.31 mmol) prepared in Example 3.

Analysis of the collected solution one hour after the start of the reaction showed that the conversion rate of levulinic acid was 100% and the yield of γ-valerolactone was 96.6%. The reaction was subsequently performed and analysis of the collected liquid 40 hours after the start of the reaction showed that the conversion rate of levulinic acid was 100% and the yield of γ-valerolactone was 94.8%.

Example 4 (Production of Catalyst)

An amount of 3.92 g of activated carbon (granular Shirasagi C2X 8/12 manufactured by Japan EnviroChemicals, Ltd.) was impregnated with an aqueous solution obtained by dissolving 0.422 g of ruthenium(III) chloride n-hydrate (1.6 mmol, manufactured by Wako Pure Chemical Industries, Ltd.) and 0.283 g of palladium(II) chloride (1.6 mmol, manufactured by Wako Pure Chemical Industries, Ltd.) in 8.0 g of 1 mol/L hydrochloric acid, and the whole was dried at 110° C. for 12 hours and then fired at 200° C. for four hours, thus obtaining 4.65 g of catalyst (hereinafter, also referred to as "Ru—Pd/AC (1) catalyst") in which 3.5% ruthenium and 3.6% palladium were supported on activated carbon.

Example 4-A (Synthesis of γ-Valerolactone)

Reaction was performed in the same manner as in Example 1 except that the catalyst to be filled was 2.0 mL (Ru: 0.31 mmol, Pd: 0.31 mmol) of Ru—Pd/AC (1) catalyst prepared in Example 4.

Analysis of the collected solution one hour after the start of the reaction showed that the conversion rate of levulinic acid was 99.4% and the yield of γ-valerolactone was 96.1%. The reaction was subsequently performed and analysis of the collected liquid 40 hours after the start of the reaction showed that the conversion rate of levulinic acid was 92.3% and the yield of γ-valerolactone was 91.6%.

Example 5 (Production of Catalyst)

An amount of 3.93 g of activated carbon (granular Shirasagi C2X 8/12 manufactured by Japan EnviroChemicals, Ltd.) was impregnated with an aqueous solution obtained by dissolving 0.422 g of ruthenium(III) chloride n-hydrate (1.6 mmol, manufactured by Wako Pure Chemical Industries, Ltd.) and 0.427 g of rhodium(III) chloride trihydrate (1.6 mmol, manufactured by Wako Pure Chemical Industries, Ltd.) in 8.0 g of 1 mol/L hydrochloric acid, and the whole was dried at 110° C. for 12 hours and then fired at 200° C. for four hours, thus obtaining 5.06 g of catalyst (hereinafter, also referred to as "Ru—Rh/AC (1) catalyst") in which 3.2% ruthenium and 3.2% rhodium were supported on activated carbon.

Example 5-A (Synthesis of γ-Valerolactone)

Reaction was performed in the same manner as in Example 1 except that the catalyst to be filled was 2.0 mL of Ru—Rh/AC (1) catalyst (Ru: 0.31 mmol, Pd: 0.31 mmol) prepared in Example 5.

Analysis of the collected solution one hour after the start of the reaction showed that the conversion rate of levulinic acid was 100% and the yield of γ-valerolactone was 96.5%. The reaction was subsequently performed and analysis of the collected liquid 40 hours after the start of the reaction showed that the conversion rate of levulinic acid was 100% and the yield of γ-valerolactone was 98.9%.

Example 6 (Production of Catalyst)

An amount of 3.93 g of activated carbon (granular Shirasagi C2X 8/12 manufactured by Japan EnviroChemicals, Ltd.) was impregnated with an aqueous solution obtained by dissolving 0.427 g of rhodium(III) chloride trihydrate (1.6 mmol, manufactured by Wako Pure Chemical Industries, Ltd.) and 0.560 g of iridium(III) chloride n-hydrate (1.6 mmol, manufactured by Sigma-Aldrich) in 8.0 g of 1 mol/L hydrochloric acid, and the whole was dried at 110° C. for 12 hours and then fired at 200° C. for four hours, thus obtaining 4.79 g of catalyst (hereinafter, also referred to as "Rh—Ir/AC (1) catalyst") in which 3.3% ruthenium and 6.3% rhodium were supported on activated carbon.

Example 6-A (Synthesis of γ-Valerolactone)

Reaction was performed in the same manner as in Example 1 except that the catalyst to be filled was 2.0 mL of Rh—Ir/AC (1) catalyst (Rh: 0.31 mmol, Ir: 0.31 mmol) prepared in Example 6.

Analysis of the collected liquid one hour after the start of the reaction showed that the conversion rate of levulinic acid was 100% and the yield of γ-valerolactone was 99.9%. The reaction was subsequently performed and analysis of the collected liquid 40 hours after the start of the reaction showed that the conversion rate of levulinic acid was 100% and the yield of γ-valerolactone was 99.4%.

Example 7-A (Synthesis of γ-Valerolactone)

A reaction tube (10 mm diameter×100 mm length) was filled with 5.0 mL of catalyst (Ru—Ir/AC catalyst) (Ru: 0.78 mmol, Ir: 0.78 mmol) produced in Example 2 and further filled, on top of the catalyst, with 3.0 mL of glass beads of 2 mm size as a preheating layer. The reaction tube was heated at 200° C. for two hours by a heater while hydrogen was supplied at 20 mL/min. Thereafter, the heater temperature was changed to 140° C., methyl levulinate was supplied at a rate of 30 mg/min into the reaction tube while hydrogen was supplied at a rate of 20.0 mL/min, and a liquid from the exit of the reaction tube was collected.

Analysis of the collected liquid one hour after the start of the reaction showed that the conversion rate of methyl levulinate was 100% and the yield of γ-valerolactone was 99.5%. The reaction was subsequently performed and analysis of the collected liquid 40 hours after the start of the reaction showed that the conversion rate of methyl levulinate was 100% and the yield of γ-valerolactone was 99.1%.

From the above results, with the use of the catalyst of the present invention, γ-valerolactone can be obtained with high productivity from a levulinic acid compound.

INDUSTRIAL APPLICABILITY

According to the present invention, γ-valerolactone can be produced with high productivity from a levulinic acid compound while the elution of metallic components can be reduced. The resultant γ-valerolactone is useful, for example, as a raw material for polymers, such as polyester and polyurethane, a resin additive, a raw material for pharmaceutical or agrochemical intermediates, or various kinds of solvents.

The invention claimed is:

1. A method for producing γ-valerolactone, the method comprising:
bringing a levulinic acid compound represented by the following formula (1),

[Chem. 1]

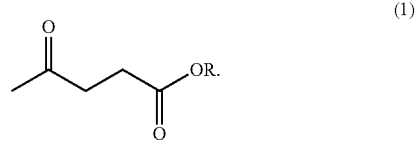

(1)

where R represents a hydrogen atom, a linear alkyl group of 1 to 6 carbon atoms or a branched alkyl group of 3 to 6 carbon atoms, into contact with hydrogen in the presence of a catalyst in which two or more different kinds of metals of Group VIII to Group X metals in the periodic table are supported on a support, thus synthesizing γ-valerolactone; wherein
the two or more different kinds of metals of Group VIII to Group X metals in the periodic table are a combination of ruthenium and iridium, or a combination of ruthenium, iridium, and one or more kinds of metals of Group VIII to Group X metals other than ruthenium and iridium.

2. The method for producing γ-valerolactone according to claim 1, wherein the support is made of silica, alumina, activated carbon or zeolite.

3. The method for producing γ-valerolactone according to claim 1, wherein
when a single kind of metal is supported on the support, the single kind of metal is supported in an amount of 0.1 to 15% by mass on the support; and
when two or more kinds of metals are supported on the support, the two or more kinds of metals are supported in a total amount of 0.2 to 30% by mass on the support.

4. The method for producing γ-valerolactone according to claim 1, wherein a reaction temperature is 50° C. to 220° C. and a reaction pressure is, in terms of hydrogen partial pressure, ordinary pressure to 10 MPa.

* * * * *